United States Patent
Hallin

(10) Patent No.: US 9,958,423 B2
(45) Date of Patent: May 1, 2018

(54) SIMULATION OF A CHROMATOGRAPHIC RUN

(71) Applicant: Biotage AB, Uppsala (SE)

(72) Inventor: Erik Hallin, Storvreta (SE)

(73) Assignee: BIOTAGE AB, Uppsala (SE)

( * ) Notice: Subject to any disclaimer, the term of this patent is extended or adjusted under 35 U.S.C. 154(b) by 732 days.

(21) Appl. No.: 14/384,292

(22) PCT Filed: Jan. 18, 2013

(86) PCT No.: PCT/EP2013/050935
§ 371 (c)(1),
(2) Date: Sep. 10, 2014

(87) PCT Pub. No.: WO2013/139496
PCT Pub. Date: Sep. 26, 2013

(65) Prior Publication Data
US 2015/0046134 A1    Feb. 12, 2015

Related U.S. Application Data

(60) Provisional application No. 61/614,799, filed on Mar. 23, 2012.

(30) Foreign Application Priority Data

Mar. 23, 2012   (EP) .................................... 12161056

(51) Int. Cl.
*G06F 17/13*   (2006.01)
*G01N 30/00*   (2006.01)
(Continued)

(52) U.S. Cl.
CPC ......... *G01N 30/8693* (2013.01); *G06F 17/13* (2013.01); *G06F 17/5009* (2013.01)

(58) Field of Classification Search
CPC .................................. G06F 17/13; G06F 19/16
See application file for complete search history.

(56) References Cited

U.S. PATENT DOCUMENTS

| 4,824,446 A * | 4/1989 | Mowery, Jr. ....... G01N 30/8693 |
| | | 422/89 |
| 2010/0004907 A1* | 1/2010 | Kidal ...................... C07K 1/16 |
| | | 703/2 |

(Continued)

FOREIGN PATENT DOCUMENTS

| JP | 2008-196963 A | 8/2008 |
| WO | WO-2011021198 A2 | 2/2011 |
| WO | WO-2011094264 A1 | 8/2011 |

OTHER PUBLICATIONS

Czok et al., "The Physical Sense of Simulation Models of Liquid Chromatography: Propagation through a Grid or Solution of the Mass Balance Equation" (1990), Anal. Chem., vol. 62, pp. 189-200 [retrieved from http://pubs.acs.org/doi/pdf/10.1021/ac00201a020].*

(Continued)

*Primary Examiner* — Brian W Wathen
(74) *Attorney, Agent, or Firm* — Harness, Dickey & Pierce, P.L.C.

(57) ABSTRACT

The present invention relates to a method for simulating a chromatographic run on a chromatograph (5) with a computation device (3) comprising at least one processor (7) and an associated digital memory (9), wherein the chromatographic run uses a mobile phase (31) comprising a mixture of at least two eluent constituents having different chromatographic properties and forming an eluent profile (33). The invention also relates to a computer program for performing the method, and an apparatus comprising a computation device and a chromatograph for performing the method.

15 Claims, 2 Drawing Sheets

(51) Int. Cl.
*G01N 30/86* (2006.01)
*G06F 17/50* (2006.01)

(56) References Cited

U.S. PATENT DOCUMENTS

2012/0179389 A1    7/2012  Reisfeld et al.
2013/0024133 A1*   1/2013  Chen .................... G06F 19/704
                                                        702/25

OTHER PUBLICATIONS

Japanese Office Action dated Oct. 28, 2016 issued in corresponding Japanese Application No. 2015-500802 (with English translation).
Karlsson D et al., "Methodologies for model calibration to assist the design of a preparative ion-exchange step for antibody purification", Journal of Chromatography, Elsevier Science Publishers B.V, NL, vol. 1033, No. 1, Apr. 9, 2004, pp. 71-82.
Anonymous, "gPROMS Introductory User Guide", Process Systems Enterprise Ltd, Jun. 2004, pp. 0-52.
Jandera et al., "Can the theory of gradient liquid chromatography be useful in solving practical problems?", Journal of Chromatography, Elsevier Science Publishers B.V, NL, vol. 1126, No. 1-2, Sep. 8, 2006, pp. 195-218.
Karlsson D et al., "Model-based optimization of a preparative ion-exchange step for antibody purification", Journal of Chromatography, Elsevier Science Publishers B.V, NL, vol. 1055, No. 1-2, Nov. 5, 2004, pp. 29-39.
Degerman M et al., "Constrained optimization of a preparative ion-exchange step for antibody purification", Journal of Chromatography, Elsevier Science Publishers B.V, NL, vol. 1113, No. 1-2, Apr. 28, 2006, pp. 92-100.
International Search Report PCT/ISA/210 for International Application No. PCT/EP2013/050935 dated Feb. 26, 2013.

* cited by examiner

SIMULATION OF A CHROMATOGRAPHIC RUN

TECHNICAL FIELD

The present invention relates to a method, a computer program and an apparatus comprising a computation device for simulating a chromatographic run on a chromatograph.

PRIOR ART

Chromatography is a chemical technique used to separate one or more compounds of a sample for analytical or preparatory purposes. The sample is supplied to a stationary phase, for example a silica gel, and a mobile phase comprising an eluent is made to flow across the stationary phase. Depending on the polarity and size of the molecules in the sample, a part of which is adsorbed to the stationary phase while another part is dissolved in the mobile phase. The relative fraction of each compound residing in the mobile phase, also known as the retardation factor (R), coupled with the flow rate of the mobile phase induces different movement rates for different compounds across the stationary phase, which results in their separation.

One problem with chromatography is to ensure that two or more compounds are properly separated. Another problem is to estimate the maximum load, or amount of sample, that can be loaded onto a specific column and still achieve a sufficient separation. Yet another problem is to minimize the cost of performing a chromatographic run, both in terms of time and in terms of costs for chemicals. In particular, for polar chromatography the cost of the eluent constituents in the mobile phase may be substantial. Hence there is a need to predict the outcome of a chromatographic run before performing the run in practice.

In "Can the theory of gradient liquid chromatography be useful in solving practical problems?" P. Jandera, J. of Chromatography A. 1126(2006)195-218, there is shown an overview of analytical models for computing the outcome of a chromatographic run in reverse or polar phase when using a gradient eluent. In particular, Jandera discloses using retention factors k measured for the stronger of two eluent constituents, in the formation of an analytical equation for calculating an expected elution volume for a compound (eq. 17, p. 205, column 2, line 2, in the case of normal phase) given a specific, linear gradient.

In WO2011/094264 there is shown an analytical method for calculating the outcome of a chromatographic run involving measurement of two isocratic (constant eluent mix) retention factors (k) from two previous TLC-runs for each compound to be analyzed in respect of the stronger eluent in the mixture, modifying the retention factor (k) with an optimum retention factor $k_{opt}$, and computing a start gradient solvent volume concentration and an end gradient solution volume concentration based on said analytical equation disclosed in Jandera. WO2011/094264 also shows checking a calculated elusion volume relative to a number of fixed conditions, and changing the start gradient solvent volume concentration and the end gradient solution volume concentration in directions known to result in better separation until the peaks satisfies said conditions.

One problem with these approaches is that only a small class of chromatographic systems, which directly fit the selected analytical model, can be modelled. Yet another problem is that it may be difficult for a user to supply adequate, accurate and sufficiently many input values for the parameters required by the model. For the method described in WO2011/094264 two measurements of the R-values for each of the compounds in the sample at two different solvent concentrations are required, which are measurements that may not be available at a reasonable cost or effort. Yet another issue is that the methods can only calculate an acceptable solution to a chromatographic run, which solution may in actuality be far from an optimal solution. For example, it may be that two compounds could be eluted closer to each other than calculated.

SUMMARY OF THE INVENTION

One objective of the present invention is to allow simulation of a chromatographic run so as to take a desired outcome for the chromatographic run into consideration.

Another objective of the present invention is to allow simulation of a chromatographic run in response to manual input concerning a desired outcome.

Another objective of the present invention is to indicate a method for simulation of a chromatographic run in response to manual input concerning a desired outcome, and so as to admit presentation of the result from the simulation in real-time.

According to a first aspect of the invention at least one of these objectives is achieved with a method according to claim 1. According to a second aspect of the invention at least one of these objectives is achieved with a computer program according to claim 14. According to a third aspect of the invention at least one of these aspects is also achieved with an apparatus according to claim 15.

According to the invention a chromatographic run on a chromatograph is simulated with a computation device comprising at least one processor and an associated digital memory, wherein the chromatographic run uses a mobile phase comprising a mixture of at least two eluent constituents having different chromatographic properties and forming an eluent profile. The invention further comprises:

storing information in the digital memory pertaining to a chromatographic model comprising mathematical equations for simulation of the chromatographic run, the mathematical equations comprising a system of differential equations modelling
  a) a progression of the eluent profile of the mobile phase relative to a stationary phase in the chromatograph,
  b) a relative distribution of a compound between the stationary phase and the mobile phase based on the local eluent profile at the location of the compound, and
  c) elution of the compound relative to the stationary phase based on the progression of the eluent profile and on said relative distribution, and simulating the chromatographic run by the at least one processor executing a computation of the chromatographic model so as to obtain a simulated peak position for the at least one compound.

One embodiment of the invention further comprises
storing a trade-off function for at least two variables simulated in the chromatographic model in the digital memory,
storing desired values for the at least two variables and storing numerical weights ascribed to any deviations from the desired values for said variables in the digital memory, simulating the chromatographic run by the at least one processor executing a computation of the chromatographic model so as to obtain simulated values for said at least two variables, and executing an optimization with the at least one processor for optimizing the trade-off function so as to minimize the weighted deviations.

By using a trade-off function defining weights for any deviations for a set of variables it is possible to balance the variables relative to each other. Hence it is possible to give a best fit, even for situations that are not physically possible to achieve. Preferably the invention also comprises estimating and displaying a measure of the errors from the desired values. Yet another advantage of using a trade-off function is that it is easier to optimize the chromatographic simulation, resulting amongst others in a decreased burden of calculation, and also in an increased freedom in which variables can be optimized and under what conditions. The trade-off function thus introduces a dynamical tolerance limit for the two or more variables, wherein the weighted sum of the dynamical tolerance limits are minimized.

Preferably, at least one of said simulated variables comprises a simulated peak position for a compound intended to be eluted in the chromatographic run. According to yet another preferred embodiment the at least two simulated variables comprises two simulated peak positions for two different compounds. Hence it is possible to assign different importance to different peaks, so that for example, it is possible to ensure a good separation between the peaks and optimize for fast elution of one of the compounds, while completely disregard for the elution of the second (or more) compound(s). This is advantageous in case of optimising production or purification of one or more compounds.

By using a set of differential equations as the chromatographic model when simulating a chromatographic run a larger number of parameters may be used as unknowns or may be simulated simultaneously, giving a model having a larger number of degrees of freedom. Thus more general chromatographic situations and conditions may be evaluated with the simulation. In particular, it is not necessary to specify as many variables as when using an analytical approach, and also, the number, nature, and quality of input values to the model may vary dependent on availability, costs and needed accuracy. Similarly, by using a set of differential equations as the chromatographic model the number and nature of the simulated output variables and values from the model may also change dependent on the information sought. It is also possible to simulate a chromatographic run based on new combinations of input or on desired parameters of the model, allowing for simulation of new aspects, which an analytical model would be unable to evaluate. Hence a user gains more freedom when setting up a particular chromatographic model. Also, it is possible to determine arbitrary changes to or improvements in the chromatographic run and then simulate which conditions that may achieve these changes and improvements.

By simulating the progression of the eluent profile of the mobile phase relative to a stationary phase in the chromatograph it is possible to evaluate the proportions of the eluent constituents at any time and at any location in the stationary phase. This step may also include simulation of the difference in flow rate between different eluent constituents in the mobile phase depending on their different tendencies to be adsorbed themselves onto the stationary phase, a phenomena that tends to distort the eluent profile. By simulating the relative distribution of a compound between the stationary phase and the mobile phase based on the local eluent profile at the location of the compound the strength of the eluent, or correspondingly, the mobility of the compound may be evaluated, in particular in combination with the simulation of the eluent profile. This step may also include compound-compound interactions, in that the presence of a compound in the mobile phase may itself change the strength of the mobile phase, in particular in the case of overloading and breakthrough. By simulating the elution of the compound relative to the stationary phase based on the progression of the eluent profile and on said relative distribution the peak position for the compound may easily be simulated by integrating over the elution of the compound based on the progression of the chromatographic run.

For the purpose of the present application, and to ensure a clear and concise terminology, the following definitions are adhered to throughout this application. It is stressed that these definitions are not necessarily commonly adopted and may be defined in another way if found in sources outside of this application.

The mobile phase is here defined as all components moving across the stationary phase, including the eluent and any compounds dissolved in or soluted by the eluent. The eluent in turn is defined to comprise all fluids (eluent constituents) that are driven to flow across the stationary phase, normally by some driving force, such as by pumping, gravity or capillary action, and not including the compounds in the sample. A constituent of the eluent is here defined as one fluid component of the eluent, thus comprising but one chemical component or complex, normally in a fluid state (gaseous or liquid).

The strength of the mobile phase, or the strength of an eluent constituent in the mobile phase, is defined as the capacity of the mobile phase or eluent constituent to elute the molecules of a compound. Strength may also be expressed in terms of the retention factor (as defined below). Normally, an eluent constituent A in a system with a given type of stationary phase is weaker than a stronger eluent constituent B if constituent B has a relative polarity closer to the polarity of the stationary phase. Such an eluent constituent B has a greater affinity for the limited number of adsorption sites on the stationary phase, meaning that there is more competition for the adsorption sites so that a larger fraction of the compounds reside in the mobile phase, thus inducing a faster elution time. The strength can also incorporate other parameters such as the size of the molecules, viscosity, stereoscopic properties, temperature, dissolved components, such as salts etc.

An eluent profile is defined to comprise information on the proportions (c) of the eluent constituents in the mobile phase as introduced into the chromatograph at given moments of the chromatographic run. The proportion may be given as concentrations, molar ratios, volume ratios, weight ratios, or similar measured in for example per cent, mole, or grams or some other suitable unit. In the case of an eluent comprising only two eluent constituents it is sufficient that the eluent profile is given as the proportion of one of the constituents, and in general, if the eluent comprises N constituents it is sufficient that the eluent profile is given as N−1 known proportions. The eluent constituents in a mobile phase that forms the eluent profile are normally selected to have different chromatographic properties, such as different polarity and viscosity, and thus have different strengths. Preferably the eluent profile also includes information on the strength of one or more of the eluent constituents in the mobile phase, wherein the eluent profile may also comprise information on the total strength of the mobile phase. The eluent profile may optionally also comprise information on other factors that may affect the strength of the mobile phase. The eluent profile preferably also includes information on changes in the proportion as a function of the progression of the chromatographic run.

The progression of the chromatographic run may include any parameter that reflects the carrying out of the chromatographic run. In a preferred embodiment the progression of the chromatographic run includes one or more of the runtime for performing the chromatographic run, the volume of mobile phase or eluent that has hitherto been introduced into the chromatograph, such as the volume of eluent pumped, or the volume of mobile phase or eluent induced to move across the stationary phase. These parameters are in turn connected to each other via flow rate for the solvent and the volume of mobile phase that can reside within the stationary phase (which volume is commonly named the column volume). One preferred unit for measuring the progression of the chromatographic run is column volumes pumped, or alternatively, relative column volumes. In a preferred embodiment the eluent profile comprises information on the proportion of the strongest eluent in the mobile phase as a function of the amount of mobile phase or eluent introduced in terms of column volumes (or alternatively as the distance travelled by the solvent front in case of TLC).

The progression of the eluent profile is in turn defined as the movement of the eluent profile across the stationary phase. The progression of the eluent profile is thus also dependent on the flow rate of the mobile phase and on the column volume, and may be given as a local eluent profile (or local eluent proportion) at a given location of the stationary phase as a function of the present progression of the chromatographic run.

The relative distribution of a compound between the stationary and mobile phases may be given by any measure measuring proportion, share, ratio or concentration. Preferably, however, the relative distribution is simulated by a model for a retardation factor or retention factor. The terms retardation factor and retention factor adheres to the definitions given by IUPAC.

The term peak position for a specific compound refers to its position in a chromatographic diagram, and is defined as the centre of the detection peak for that compound in terms of a parameter measuring the progression of the chromatographic run. The peak position can thus be given in terms of time, amount of mobile phase introduced measured in column volumes or similar measures of chromatographic progression, depending on a user's preferences. The physical significance of the peak position corresponds to the detection peak for that compound when eluted. The volume of mobile phase required to elute one half of a compound (corresponding to the middle of the detection peak) out of the stationary phase, the elution volume, can also be expressed in terms of the retardation factor, which is related to the amount of surplus mobile phase (in column volumes) needed to make a compound move out of the stationary phase in an isocratic chromatographic run.

The model preferably also includes predicting the ratio or proportions between the eluent constituents in the mobile phase anywhere at any time in the column. Preferably the model also comprises information on the flow rate of the mobile phase. The model further models mobility based on the distribution of each compound between the mobile phase and the stationary phase. These parameters may be obtained from a variety of sources, including tabulated values or measured values from experiments.

In a preferred embodiment the invention comprises
receiving input from a user on a desired value for a peak position for at least one compound to be eluted,
simulating the chromatographic run by the at least one processor executing a computation of the chromatographic model so as to obtain a correspondence between the peak position for the compound and an eluent profile for the mobile phase, and
varying the simulation so as to predict an eluent profile for the mobile phase resulting in a simulated peak position being within a tolerance limit of the desired peak position.

Thus it is possible for a user to state a desired peak position for at least one compound in a chromatographic run and receive a simulated result stating the conditions necessary to obtain that peak position.

In an alternative embodiment the invention also comprises
presenting a simulated peak position for at least one compound and its associated eluent profile on a display, and
providing a user interface for receiving information from a user on desired changes to one or more of the simulated peak position and to the eluent profile.

Thus it is possible for a user to change the peak position for one or more compounds in real time and almost directly receive feedback on how the conditions for the chromatographic run must be changed in order to obtain that or these peak position(s). Similarly, the user may also receive information on how a change in one peak position necessarily leads to a change in another peak position. It is also possible for a user to change the initial conditions for a chromatographic run and to directly receive feedback on how this changes the peak positions.

According to one embodiment the invention comprises
providing a user interface for receiving information from a user on desired changes to at least two simulated peak positions,
simulating the chromatographic run by the at least one processor executing a computation of the chromatographic model so as to obtain a correspondence between the peak positions for the at least two compounds and an eluent profile for the mobile phase, and
varying the simulation so as to predict an eluent profile for the mobile phase resulting in that the two or more simulated peak positions are within a tolerance limit of their respective, desired peak positions. Hence, it is possible to simulate which eluent profile that may result in desired values for two or more peak positions. Hence it is possible for a user to directly control the desired separation of and/or the elution volume for two or more compounds.

According to one embodiment the invention comprises simulating the chromatographic run by simulating the peak positions for the at least two compounds as zero-dimensional points. By relinquishing a simulation of the diffusion and broadening of the peaks the computational burden is substantially decreased. In one embodiment the invention comprises simulating the peak positions as zero-dimensional points in a first simulation of the chromatographic run, and then simulating diffusion and broadening of the peaks in a second simulation. Thus the diffusion can be simulated as a perturbation of the first simulation run, which also leads to a decreased computational burden. In yet another embodiment the invention comprises simulating the chromatographic run by simulating the peak positions as being within an interval of a limited width. Thus the simulation comprises simulation of a limited amount of diffusion broadening, by simulating only a limited width of the column, which also limits the number of computations needed relative to simulating the chromatographic run at all points of the column.

According to one embodiment the invention further comprises receiving input from a user interacting with the computation device on a desired value for at least one of said at least two variables, and executing an optimization of the trade-off function with the at least one processor based on the new input value.

Thus it is possible to receive arbitrary changes to or improvements in the chromatographic run from a user and then simulate which conditions that may achieve these changes and improvements. This may be carried out both in terms of desired outcomes, such as peak position, and in terms of desired conditions, such as a desired eluent profile or desired eluent proportions.

According to a preferred embodiment the method comprises simulating a chromatographic run on a normal phase chromatograph column. Simulating or performing calculations of a chromatographic model in normal phase is considered much more difficult and more unstable than calculating and simulating a reversed phase chromatographic run. With the invention however, it has been realised that the method proposed is almost equally excellent in simulating a chromatographic run on a normal phase column.

Preferably the invention comprises receiving information on measured retardation factor values (R) and/or retention factor values (k) from previous chromatographic runs. Preferably the measured values are obtained from isocratic runs. If receiving values for measured retardation factors the method preferably comprises converting the received retardation factor (R) into retention factors (k), preferably by using the equation $k=(1-R)/R$. The method further comprises forming a model for the retention factor k comprising fitting the received, measured values to the model: $k=(a+bc)^{-m}$. where a, b and m are arbitrary parameters of the model, and which are to be determined, and c is the proportion of a strong eluent constituent in the mobile phase. In case the number of measured values of R (or k) is insufficient to determine all parameters in the model, the method comprises setting one or more of the parameters in the model to a neutral value. For example, in case only one measured value is received the method may comprise setting 'a' to zero and 'm' to one. Preferably the invention also comprises receiving retardation factor values (R) from previous chromatographic runs on TLC plates. By receiving the retardation factor values from measurements on TLC-plates a low cost is ensured, since runs on TLC-plates are normally very fast and inexpensive. However, if available, the invention may also include receiving and using the values from one or more measurements from (isocratic or gradient) LC runs, which are probably more accurate than if using values based on measurements on TLC-plates.

According to one embodiment the invention comprises
receiving one or more values of the retardation factor (R) or retention factor (k) as measured on a first chromatographic system,
using a correction factor (a) to correct for differences between the first chromatographic system and a second chromatographic system when estimating the at least one parameters of the retention factor model, and
simulating the chromatographic run on the second chromatographic system.

The correction factor is preferably determined experimentally for each pair of chromatographic systems. Preferably one or more correction factors are stored in the memory, and a suitable correction factor is selected dependent on the chromatographic systems from which the measurement values are obtained and on the chromatographic system on which the simulation is to be performed. The correction factor a may adjust for differences between the systems that may affect the chromatography performance, such as form factor, pack density, solid phase particle quality and sizes, fluid drive system and other differences. In particular the correction factor is advantageous to include if obtaining the measured values on a TLC-plate while simulating on an LC-column.

According to one embodiment the invention comprises controlling a chromatographic run on a chromatograph, by
receiving information from a user on a selected simulated eluent profile desired to be run on the chromatograph, and
controlling the chromatograph to run a sample on the chromatograph with a mobile phase having an eluent profile corresponding to the selected, simulated eluent profile.

Hence there is no need to manually transfer the results and conditions from a simulated chromatographic run to the chromatograph to perform the chromatographic run, but the apparatus and the computation device performs the chromatographic run automatically.

BRIEF DESCRIPTION OF THE ATTACHED DRAWINGS

The invention is now to be described as a number of non-limiting examples of the invention and with reference to the attached drawings.

DETAILED DESCRIPTION

Figure 1:
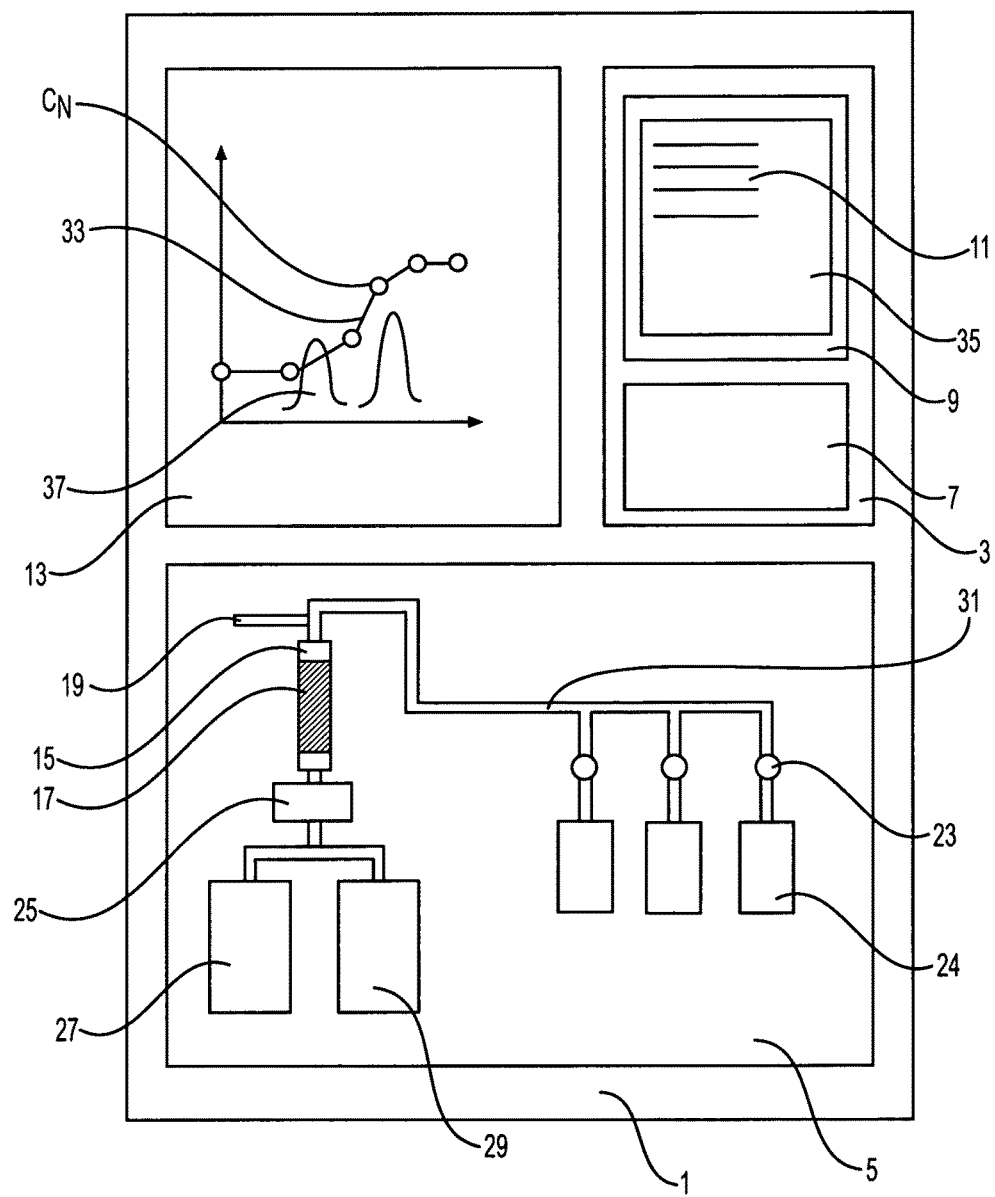
FIG. 1 shows an apparatus comprising a computation device and a chromatograph according to one example of the invention.

In FIG. 1 an apparatus 1 comprising a computation device 3 and a chromatograph 5 is shown. The computation device comprises a processor 7 and an associated digital memory 9. The processor is arranged to process computer program instructions 11 stored in the digital memory, and to receive and transfer signals to the chromatograph and to one or more I/O-units, in this example to at least one display 13. The chromatograph comprises a column 15 packed with a stationary phase 17 that can be polar (termed a normal phase), non-polar (termed a reverse phase), or have some other form of selectivity. The chromatograph further includes a sample introduction port 19, one or more inlets 24 for eluent constituents of a mobile phase, one or more drives 23 for driving a flow of the mobile phase, such as pumps, a detector connected at the downstream end of the column, and a waste outlet 27 or collector 29.

In operation a sample comprising one or more compounds is introduced into the sample port 19. The drives 23, in this example the pumps, drive the constituents forming the eluent of the mobile phase to flow through the chromatograph. The mobile phase carries the sample to and through the column 15. Due to differences in polarity and differences in selectivity the proportion of each compound being in the mobile phase 31 relative to being adsorbed to the stationary phase differs between compounds. This leads to a separation of the compounds during their travel through the column due to their different movement rates. The compounds may then be detected by the detector 25, and may be carried to the waste outlet 27 or be collected in the collector 29 for further processing or use.

The chromatograph 5 is in this example illustrated by a simple, liquid chromatography (LC) chromatograph, but it could in principle be constituted by any other type of chromatograph, such as a flash chromatograph, a high performance liquid chromatograph, or similar. Furthermore, the column 15 is preferably packed with a polar stationary phase, forming a normal phase chromatograph, which is particularly suited to the ensuing method. The material of the stationary phase could then be for example a silica gel, or any other polar or hydrophilic stationary phase known in the art. Alternatively, the column could be a reverse phase column and the material of the stationary phase could then be a modified silica gel, a polymer, such as styren or some other non-polar material known in the art. The chromatograph is further arranged to be able to operate at least one chromatographic run with a mobile phase 31 comprising a mixture of at least two eluent constituents having different chromatographic properties and forming an eluent profile 33. The eluent profile comprises the relative proportions of the participating eluent constituents forming the mobile phase as introduced relative to the progression of the chromatographic run, such as at different runtimes, or alternatively, as measured by the hitherto total volume of mobile phase pumped. The use of column volume or run time as the measure of progression of the chromatographic run is optional and related to each other through the flow rate of the mobile phase and the column volume.

The digital memory 9 of the computation device 3 comprises program instructions 11 stored therein forming a computer program 35, and which are intended to be executed by the processor and to control the actions of the processor. The computer program is in this example arranged to induce the processor to perform the method as described in relation to FIGS. 2-3. The computer program 35 is further arranged to control the operation of the chromatograph 5.

Figure 2:
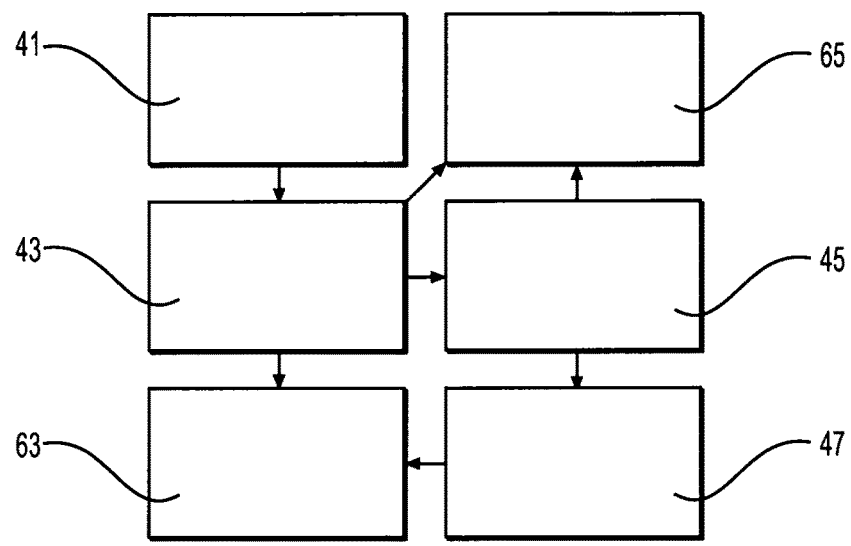
FIG. 2 shows a flowchart of a method according to one example of the invention.
Figure 3:
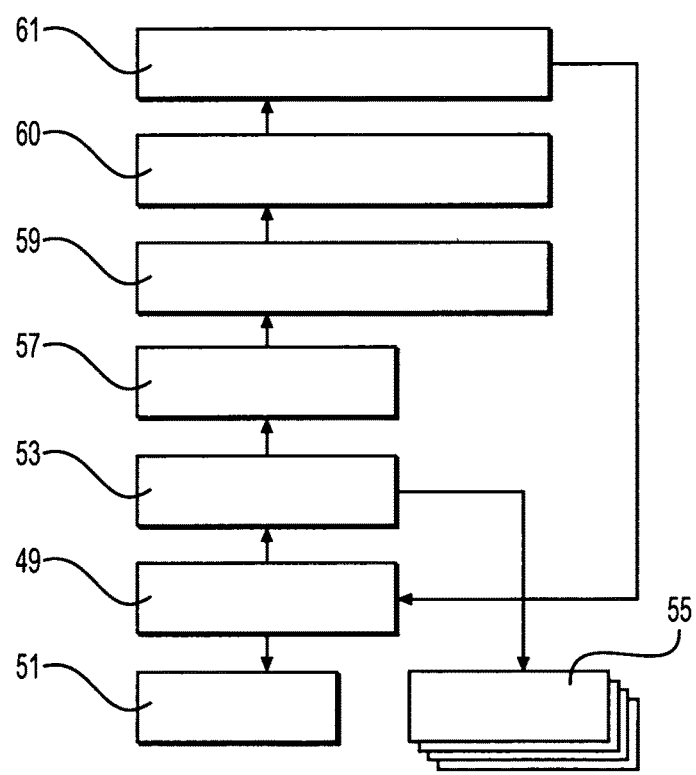
FIG. 3 shows a computer implementation of the numerical calculation of the model.

In FIGS. 2-3 a method for simulating a chromatographic run on the chromatograph 5 with the computation device 3 according to the present invention is shown. FIG. 2 shows a flowchart over an operating structure for the computer program 35. Depending on the purpose of and the conditions for performing a chromatographic run the order of performing the different steps of the method as described in relation to FIG. 2, as well as which steps to be included, and which parts of each step is to be performed, may differ between executions. FIG. 3 in turn shows a flowchart of the various mathematical and numerical functions that may be performed during numerical execution of the chromatographic model.

In an initiation step 41 the method comprises storing information in the digital memory 9 pertaining to a chromatographic model comprising mathematical equations for simulation of the chromatographic run. According to the invention the mathematical equations comprises a system of differential equations modelling a) a progression of the eluent profile 33 of the mobile phase 31 relative to a stationary phase 17 in the chromatograph 5, b) a relative distribution of a compound between the stationary phase and the mobile phase 31 based on the local eluent profile 33 at the current location of the compound, and c) elution of the compound relative to the stationary phase 17 based on the progression of the eluent profile 33 and on said relative distribution.

The model may be stored in the form of a set of program instruction, a set of proper mathematical equations or a combination thereof. The term storing is intended to include both downloading of the model into the digital memory 9, such as loading a computer program into the digital memory, and providing a digital memory with the model already written therein. The digital memory 9 may be a cache memory of the processor, a random access memory, a flash memory, a hard disk or an auxiliary memory which may be accessed by the processor 7.

In the initiation step 41 the method also comprises storing a trade-off function for at least two variables simulated in the chromatographic model in the digital memory. Preferably, the method comprises storing a trade-off function for a suitable number, preferably more than two, of the variables in the model. In a particularly useful example the trade-off function relates to two or more peak positions 37 for two or more compounds. The trade-off function could then be defined so that the simulation is optimized with an aim to find the conditions making the simulated peak positions 37 be formed a certain distance apart, such as two column volumes apart. The weights assigned to the trade-off function could then be a weight of two for any discrepancies being in the direction of two peaks being too far apart, and a weight of twenty for any discrepancies being in the direction of two peaks being closer than said desired distance. Hence, some leeway is permitted, so that a simulation result can be obtained even if the desired outcome is impossible to form. Also, the use of a trade-off function allows for a simpler implementation of the optimization procedure. In this example, the trade-off function could in principle also include variables describing the conditions for performing a chromatographic run, such as information on the elution profile, temperature, and other factors that may affect the chromatographic run.

In an input step 43 the method comprises receiving input from a user or some other source, such as from reading a data file or from being coded in the computer program. In this example the input step 43 comprises receiving one or more values for retardation factors, R, and/or retention factors, k, measured during one or more previous chromatographic runs of that compound and with a mobile phase comprising one or more of the eluent constituents which are to be simulated, and also receiving information on the associated eluent profile of the previous chromatographic runs. It is sufficient that only one retardation or retention factor value for each compound is received. However, the more values that are available the better and more accurate simulation. In one example the method comprises receiving two measured values. In a preferred example the method comprises receiving at least three measured values for the retardation factors, R, or retention factors k, for at least one compound, together with information on its associated eluent profile. Preferably, the eluent profiles associated with the measured retardation factors comprises an eluent with constant proportions for preferably all, but at least for the strongest of the constituents of the eluent in that chromatographic run (an isocratic eluent profile), but linear gradient elution profiles are also possible to use. The retardation or retention factor may also be received as a measure of an elution column volume (LC) or as a distance travelled (TLC) for the compound, from which the retardation or retention factors may be estimated.

The input step 43 may also or alternatively optionally comprise values or information for other parameters, variables or qualitative data. For example the input may comprise information on the compounds to be simulated, and/or which eluent constituents are intended to be used in the chromatography. The method may then comprise checking a database for values of retardation factors, retention factors or other parameters. The method may further comprise receiving and storing desired values for the at least two variables of the trade-off functions, and/or storing numerical weights ascribed to any deviations from the desired values. The input step 43 may also comprise receiving information on a desired type of elution profile, such as if the elution profile should comprise two, three or more eluent constituents, the nature of the eluent constituents, and the shape of a change in the proportions between the eluent constituents, such as linear gradient, non-linear gradient, etc. Possibly, information could also be received on the nature of the stationary phase and/or of the compounds in the sample. In an alternative embodiment the input step 43 could also comprise partly or completely receiving and storing variables and/or weights of the trade-off function.

In a modelling step 45 the method comprises storing a model for a retention factor, k, of the form $k=(a+b*c)^{-m}$ in the digital memory, where a, b and m are parameters of the model. The method further comprises estimating at least one of the parameters a, b or m by fitting the at least one measured retardation or retention factor value and associated eluent proportion c into the model. In case of only having received one measured retention factor value, the method comprises calculating the parameter b, and setting a to zero and m to one. In case of only receiving two measured retention factor values the method comprises calculating the parameter b, and one of a or m, while setting the third parameter to its defined value as above. In case three or more measured retention factor values are received the method comprises estimating the parameters a, b and m by non-linear regression. Alternatively, the input received in the input step 43 may instead comprise already estimated values for the parameters a, b, and m for the model for the retention factor directly. This may happen if estimations of a, b, and m have already been performed, for example during a previous simulation attempt, or from tabulated data. Optionally, the method may comprise including a correction factor α into the model, which correction factor includes corrections for differences in form factor, pack density, particle quality, fluid drive system and other differences between the chromatographic system in which the experimental measurements of the retention and/or retardation factors are made, and the chromatographic system which is to be simulated, such as between a TLC-plate and an LC-column. The correction factor may enter into the model for k as $k=\alpha(a+b*c)^{-m}$, or the correction factor may enter as a correction to the measured retention or retardation values before they are entered into the model for calculation of a, b or m, for example as: $k_{corrected}=\alpha*k_{measured}$, where $k_{corrected}$ is used in the model instead of $k_{measured}$. The value of the correction factor α is preferably determined experimentally for each pair of chromatographic systems.

In a modelling step 45 the method further comprises storing an eluent profile vector ĉ in the digital memory comprising N vector elements, each vector element $\hat{c}_N$ comprising information on the proportion c of one of the constituents of the eluent in the mobile phase at a certain point of progression of the chromatographic run. In this example, the method also comprises associating each vector element $\hat{c}_N$ with a measure of the progression of the chromatographic run, in this example with a volume $v_N$ of eluent introduced into the chromatograph. The volume of eluent introduced is preferably measured in column volumes. In case the eluent comprises three or more constituents the eluent profile vector may correspondingly comprise a second set of proportion values for the second eluent and so on. Preferably the number N of vector elements is larger than or equal to four, allowing a description of a linear gradient. Preferably, the number N of vector elements is larger than or equal to five, allowing much more general eluent profiles. By giving the eluent profile as a vector comprising N>5 elements a very large selection of different eluent profiles may be simulated, and it is not at all necessary that the eluent profile is a linear gradient profile, nor that it consists of a constant elution proportion. Thus a wider class of chromatographic runs may be simulated. Further, the use of an eluent profile vector gives a very stable method of simulation, and allows the use of less taxing numerical methods for its solution.

In a simulation step 47 the method comprises simulating the chromatographic run by the at least one processor executing a computation of the chromatographic model so as to obtain a simulated peak position(s) for the at least one compound(s). The relationships between the numerical calculations performed during the simulation are shown in FIG. 3. Throughout this example the progression of the chromatographic run is given in terms of the present number of column volumes of mobile phase introduced, $v_P$, due to that this measure gives a simpler mathematical model. However, it should be appreciated that other measures could in principle also be used.

In a first simulation block 49 the method comprises simulating the progression of the eluent profile of the mobile phase relative to the stationary phase 17 in the chromatograph. In this example this step comprises simulating the proportions of the eluent constituents of the mobile phase at different locations of the column at different times as measured by the progression of the chromatographic run. The first simulation block 49 comprises first calling an elution profile calculation function, represented by the second simulation block 51, to receive therefrom an estimation of the present eluent profile in terms of the present eluent constituent proportions $c_{P,1\ldots i}$ being introduced into the chromatograph, preferably at the beginning of the stationary phase 17, at a point of progression of the chromatographic run, $v_P$.

The second simulation block 51 in turn comprises using information on the eluent profile vector ĉ, its vector elements $\hat{c}_N$, and the present point of progression of the chromatographic run, $v_P$, for evaluating the proportions $c_{P,1\ldots i}$ of each eluent constituent (i) at the beginning of the stationary phase at the present point of progression of the chromatographic run $v_P$. In this example the second simulation block 51 comprises interpolating the proportions $c_{P,1\ldots n}$ based on the elution profile vector elements $\hat{c}_N$, their associated elution volumes, and the present progression of the chromatographic run, thus giving the momentary proportions $c_{P,1\ldots i}$ of the eluent constituents, and returning these values to the first simulation block 49.

The first simulation block 49, further comprises estimating the local eluent profile, or eluent constituent proportions $c_{Local,1\ldots i}(v_P)$ throughout the column for each eluent constituent (i). In this example the estimation comprises simulating the progression of the eluent profile through the column, for example by use of the equation $$c_{local,1\ldots i}=c(c_{P,1\ldots i},v-z,v_P)$$

where v represents the volume of eluent introduced, and z represents the position in the column as measured in relative column volumes running from 0 to 1. Thus the progression of the elution profile across the stationary phase is obtained.

However, other equations describing the progression of the eluent profile for different configurations of a chromatograph may also be used or may replace the example above. For example, the equation may comprise a submodel for describing the flow rate in terms of gravitational force, gas pressure, pressure drop, diffusion etc., instead of incorporating the flow rate indirectly into the eluent profile vector, as well as models for other factors such as retention and adsorption of an eluent constituent onto the stationary phase.

In a third simulation block 53 the method comprises simulating the relative distribution of a compound between the stationary phase (17) and the mobile phase (31) based on the local eluent profile, $c_{local, 1 \ldots n}$, at the present location of the compound. In this example the method comprises simulating the strength of the mobile phase locally for each compound. In this example the method comprises using the information from the first and second simulation blocks 49, 51 on the local eluent profile in combination with the model for the retention factor as described in the modelling step 45 of the model, thus obtaining the relative distribution of each compound between the stationary and the mobile phase at the location of the compound.

The third simulation block 53 thus comprises calling a retention factor calculation function, represented by a fourth simulation block 55. In this example the fourth simulation block 55 comprises receiving the value(s) for the local proportions of the eluent constituents at the present location of the compounds $c_{local, 1 \ldots n}$ and using the model for the retention factor $k=(a+b*c)^{-m}$, which gives a direct estimate of the relative distribution of the compound between the stationary phase and the mobile phase. In this example, in the case of an eluent profile having only two eluent constituents, the distribution may be evaluated by the equation of the form:

$$k_{Local, 1 \ldots j} = (a_j + b_j * c_{local, 1 \ldots i})^{-mj},$$

for each compound j, and with the parameters a, b, m as fitted in the modelling step 45. However, the expression in the fourth simulation block may optionally also comprise other factors or parameters that may affect the distribution of each compound j. Thus the method comprises simulating the relative distribution of the compound between the stationary phase and the mobile phase based on the model for the retention factor (k) and the local eluent profile at the location of the compound.

In a fifth simulation block 57 the method comprises simulating an elution of the compound relative to the stationary phase based on the progression of the eluent profile from block 49 and on said relative distribution from step 53 and 55. In this example the fifth simulation block 57 comprises simulating the movement (elution) of each compound relative to the stationary phase (column) based on the progression of the eluent profile and by taking into account the proportion $k_{Local, 1 \ldots j}$ of the compound residing in the mobile phase 31 from block 55. In this particular example the model may comprise an equation of the form:

$$dz_j/dv = 1/(1+k_{Local, 1 \ldots j}),$$

This gives a measure of the elution, or synonymously, the change in position for the compound relative to the stationary phase as measured in relative column volume (from 0 to 1). These equations thus form a set of differential equations which on computation gives the momentary progression of each compound through the chromatographic column.

The method further comprises a sixth simulation block 59 comprising simulating the chromatographic run by the at least one processor 7 executing a computation of the chromatographic model. In this example the method comprises repeating the simulation blocks 49-55 with a numerical method for solving differential equations, thus resulting in obtaining simulated resulting peak positions 37 for each of the compounds. The differential equations of block 51 to 57 may be computed by executing a numerical method for solving a system of differential equations, such as an Euler-method, Runge-Kutta method or any other numerical method for solving differential systems of equations. In this example the simulation comprises simulating the chromatographic run by the at least one processor executing a computation of the chromatographic model so as to obtain a correspondence between the resulting peak position for a compound and an eluent profile for the mobile phase, by executing blocks 49 to 57. The method thus also comprises simulating the chromatographic run with computations based on the eluent profile vector ĉ.

The method further comprises simulating the chromatographic run by the at least one processor 7 executing a computation of the chromatographic model so as to obtain simulated values for at least two variables of the trade-off function. In this example the variables of the trade-off function are set to be two peak positions. However, due to the general nature of the simulation model, it is possible to include almost any other variable or parameter of the model as the desired variables of the trade-off function as well. The method further comprises computing a weighted trade-off score based on the trade-off function. Hence a score is assigned to the point represented by the presently simulated elution profile vector ĉ, in a point space spanned by the set of all possible values for the elements $ĉ_N$ of an arbitrary elution profile vector of the same dimension.

In a seventh simulation block 60 the method comprises calculating a score for the trade-off function at said point in the point space, by summing the weighted deviations for all variables presently selected as being active variables of the trade-off function.

In an eighth simulation block 61, the method comprises executing an optimization of the simulation so as to produce an optimised chromatographic run. The optimization may comprise re-executing the simulation, such as the simulation in blocks 49-60, to obtain a plurality of simulation results, and selecting the optimum simulation result from among the plurality of simulation results. In one example the method comprises varying the simulation by re-executing the simulation (in blocks 49-60) with a varying simulation eluent profile so as to predict a resulting eluent profile (33) for the mobile phase resulting in a simulated peak position (37) being within a tolerance limit of the desired peak position. The tolerance limit may for example be a specified range about the peak position, which may be pre-defined or entered by the user in the input step 43. However, the tolerance limit may also be dynamically set as described below.

In another example the eighth simulation block 61 of the method comprises executing an optimization with the at least one processor for optimizing the trade-off function so as to minimize the sum of weighted deviations, in this example the score of the trade-off function as calculated in the seventh simulation block 60. In this example the method may comprise optimizing the value of the trade-off function by varying the eluent profile in the form of the eluent profile vector (ĉ), and re-executing the simulation in blocks 49-60 with the new, varied vector elements $ĉ_N$. The method further comprises selecting the eluent profile vector ĉ that results in the least value for the score of the trade-off function as the optimum eluent profile. Thus, the weights of the trade-off function together with selecting the simulation giving the least score dynamically sets the tolerance limits for the peak position or positions.

In this example at least one of said simulated variables of the trade-off function comprises a simulated peak position for a compound intended to be eluted in the chromatographic run. However, at least one of said variables of the trade-off function could also comprises the eluent profile ĉ and information on the proportion c of at least one of the eluent constituents in the mobile phase. Hence, the tolerances about each peak position, eluent profile vector element, and/or other variables of the trade-off function may be dynamically set to the values minimizing the score of the trade-off function.

In this example the method comprises optimizing the value of the trade-off function by the at least one processor 7 executing a numerical direct search method that varies the eluent profile vector (ĉ) and re-executes the simulation in blocks 49-60 with the new, varied vector elements $ĉ_N$. The method further comprises selecting the eluent profile vector ĉ that results in the least value for the trade-off function as the optimum eluent profile, and which also dynamically sets the tolerance limit for the peak position or positions. The direct search method preferably comprises a simplex method, such as the Nelder Mead Simplex method, that varies the vector elements $ĉ_N$. The model of the chromatographic run is not necessarily well behaved for all forms of chromatography, meaning that it is an advantage to use a direct search method, or a simplex method, which are robust methods less affected by error fluctuations.

Now returning to FIG. 2, in a presentation step 63 the method comprises presenting the simulated resulting peak position for the at least one simulated compound and its associated eluent profile on the display 13. Continuing once more to the input step 43, the method also comprises providing a user interface 13 for receiving information from a user. In this example the method comprises providing a user interface 13 for receiving input from a user on a desired value for a resulting peak position for at least one compound. The method preferably also comprises receiving information from a user on desired changes to one or more of the simulated resulting peak position and to the eluent profile. Alternatively, or in combination with, the method may also comprise receiving input from a user on one or more desired values for the eluent profile.

In this example the display is a touch screen, wherein the user may point at the screen and for example drag a simulated, displayed peak position to a new desired peak position. Similarly the user may simply point on a location of the eluent profile 33, such as on a displayed element of the eluent profile vector ($ĉ_N$), and drag the eluent profile 33 (or element of the eluent profile vector) to form a new desired eluent profile having a new proportion c for an eluent constituent, and/or to a new point of progression of the chromatographic run. Alternatively, the input could also be received from a keyboard, a computer mouse, or some other form of input device known in the field of I/O-units.

In case one of the received desired values is a variable of the trade-off function, the desired value for that parameter is changed based on the user input. In case one of the received desired values is not belonging to the trade-off function, this value and its parameter may be incorporated as a variable into the trade-off function. Hence the method comprises receiving input from a user interacting with the computation device on a desired value for at least one of said at least two parameters of the trade-off function.

The method then comprises repeating the simulation step 47 and the computations of simulation blocks 49-61, so as to execute an optimization of the trade-off function with the at least one processor based on the new input values. Hence, it is possible for a user to easily and quickly give direct input to the computation device, after having been given a first simulation result, and change it at will in order to optimize the chromatographic run in cooperation with the simulation. Hence, the skill, experience and expert knowledge of the user, and the user's knowledge on or preferences for the desired results for the chromatographic run, in combination with a general and very allowing simulation can be used in concert to give even better results than what only one of the user or the computation device could do alone.

The method further comprises a control step 65 comprising receiving information from a user on a selected simulated eluent profile 33 desired to be run on the chromatograph, and controlling the chromatograph 5 to run a sample on the chromatograph with a mobile phase having an eluent profile corresponding to the selected eluent profile 33. Thus, it is possible to simulate a chromatographic run to obtain which conditions that gives desired results, and then directly use the conditions from the simulation in order to control the chromatograph 5 to carry out a chromatographic run with these exact conditions. In this example the method also comprises a feedback step in which the results from the real chromatographic run is compared to the simulated result, and any discrepancies are evaluated for possibilities to improve the model. For example, information on the real peak position for a compound could be used to improve the parameters a, b, m of the model for the retention factor.

The invention is not limited to the examples and embodiments shown, but may be varied freely within the framework of the following claims. In particular, the different aspects and features of the examples and embodiments are not exclusive of each other, but may be combined to form new embodiments, which are considered to be within the scope of the invention.

The invention claimed is:

1. A method for operating a chromatographic run on a chromatograph, wherein the chromatographic run uses a mobile phase including a mixture of at least two eluent constituents having different chromatographic properties and forming an eluent profile, the method comprising:
   simulating the chromatographic run based on executing a computation of a chromatographic model to generate a simulated peak position of a compound associated with the simulated chromatographic run and to determine respective simulated values of at least two variables of a trade-off function, the chromatographic model including a set of differential equations that model
      a progression of the eluent profile of the mobile phase relative to a stationary phase in the chromatograph,
      a relative distribution of the compound between the stationary phase and the mobile phase based on an estimated local eluent profile at a present location of the compound, and
      an elution of the compound relative to the stationary phase based on the modelled progression of the eluent profile and on said relative distribution;
   optimizing the trade-off function associated with the at least two variables, based on repeating the simulating with varying eluent profiles, to determine an optimum eluent profile that is associated with a minimized sum of numerical weights ascribed to deviations from respective particular values of the at least two variables; and controlling the chromatograph to perform the chromatographic run, based on receiving a user-initiated selection of the optimum eluent profile, such that the chromatograph runs a sample with a mobile phase including at least the compound and having an eluent profile corresponding to the optimum eluent profile.

2. The method according to claim 1, further comprising:
receiving input from a user, the input indicating a particular value of at least one variable of the at least two variables, and
executing an optimization of the trade-off function based on the particular value of the at least one variable.

3. The method according to claim 2, wherein the at least one variable of the at least two variables includes the simulated peak position of the compound in the simulated chromatographic run.

4. The method according to claim 2, wherein the at least one variable the at least two variables is associated with the eluent profile and information indicating a proportion of at least one constituent of the at least two eluent constituents in the mobile phase.

5. The method according to claim 1, further comprising:
receiving input from a user, the input indicating a particular value of a peak position of the compound,
simulating the chromatographic run to obtain a correspondence between the peak position of the compound and the eluent profile for the mobile phase, and
repeating the simulating with varying eluent profiles to determine a particular eluent profile for the mobile phase that is associated with the simulated peak position being within a tolerance limit of the user-indicated particular value of the peak position.

6. The method according to claim 5, further comprising:
presenting the simulated peak position of the one compound and an eluent profile associated with the compound on a display, and
providing a user interface to enable receipt of information from a user, the information indicating user desired changes to one or more elements of the simulated peak positions of the compound and to the eluent profile associated with the compound.

7. The method according to claim 1, further comprising:
storing an eluent profile vector including N vector elements, each vector element including information indicating a momentary proportion c of one constituent of the eluent constituents in the mobile phase at a point of progression of the chromatographic run, and
simulating the chromatographic run with computations based on the eluent profile vector.

8. The method according to claim 7, further comprising:
optimizing a value of the trade-off function based on executing a numerical direct search method that varies the eluent profile vector and re-executes the simulation with varied vector elements of the varied eluent profile vector.

9. The method according to claim 1, further comprising:
receiving one or more measured retardation factor or retention factor values of the compound with a mobile phase including one or more constituents of the at least two eluent constituents, the one or more measured retardation factor or retention factor values associated with one or more previous chromatographic runs of the compound, and receiving information indicating an associated proportion c of at least one constituent of the at least two eluent constituents relative to a total mobile phase, storing a model of a retention factor of a form $k=(a+b*c)-m$, where a, b and m are parameters of the model, estimating at least one parameter of the parameters a, b or m based on fitting the one or more measured retardation factor or retention factor values and associated eluent proportion c into the model, and simulating the chromatographic run based on the model of the retention factor.

10. The method according to claim 9, further comprising:
receiving three or more measured retardation or retention factor values of the compound and associated proportions for at least one constituent of the at least two eluent constituents, and
estimating the parameters a, b and m based on non-linear regression.

11. The method according to claim 9, further comprising:
receiving one or more values of the retardation factor or retention factor as measured on a first chromatographic system,
using a correction factor to correct for differences between the first chromatographic system and a second chromatographic system when estimating the at least one parameters of the retention factor model, and
simulating the chromatographic run on the second chromatographic system.

12. The method according to claim 1, further comprising:
simulating the chromatographic run on a normal phase chromatograph column.

13. An apparatus, comprising:
a chromatograph configured to perform a chromatographic run using a mobile phase including a mixture of at least two eluent constituents having different chromatographic properties and forming an eluent profile; and
a computation device configured to
simulate the chromatographic run based on executing a computation of a chromatographic model to generate a simulated peak position of a compound associated with the simulated chromatographic run and to determine respective simulated values of at least two variables of a trade-off function, the chromatographic model including a set of differential equations that model
a progression of the eluent profile of the mobile phase relative to a stationary phase in the chromatograph,
a relative distribution of the compound between the stationary phase and the mobile phase based on an estimated local eluent profile at a present location of the compound, and
an elution of the compound relative to the stationary phase based on the modelled progression of the eluent profile and on said relative distribution;
optimize the trade-off function associated with the at least two variables, based on repeating the simulating with varying eluent profiles, to determine an optimum eluent profile that is associated with a minimized sum of numerical weights ascribed to deviations from respective particular values of the at least two variables; and
control the chromatograph to perform the chromatographic run, based on receiving a user-initiated selection of the optimum eluent profile, such that the chromatograph runs a sample with a mobile phase including at least the compound and having an eluent profile corresponding to the optimum eluent profile.

14. A method for operating a chromatographic run on a chromatograph, wherein the chromatographic run uses a mobile phase including a mixture of at least two eluent constituents having different chromatographic properties and forming an eluent profile, the method comprising:

performing a simulation of the chromatographic run based on executing a computation of a chromatographic model to generate a correspondence between a simulated peak position of a compound associated with the simulated chromatographic run and an eluent profile for the mobile phase;

varying the simulation to determine a particular eluent profile for the mobile phase that is associated with a simulated peak position being within a tolerance limit associated with a user-indicated particular peak position; and controlling the chromatograph to perform the chromatographic run based on the particular eluent profile, such that the chromatograph runs a sample with a mobile phase including at least the compound and having an eluent profile corresponding to the particular eluent profile.

15. An apparatus, comprising:

a chromatograph configured to perform a chromatographic run using a mobile phase including a mixture of at least two eluent constituents having different chromatographic properties and forming an eluent profile; and a computation device configured to performing a simulation of the chromatographic run based on executing a computation of a chromatographic model to generate a correspondence between a simulated peak position of a compound associated with the simulated chromatographic run and an eluent profile for the mobile phase;

varying the simulation to determine a particular eluent profile for the mobile phase that is associated with a simulated peak position being within a tolerance limit associated with a user-indicated particular peak position; and controlling the chromatograph to perform the chromatographic run based on the particular eluent profile, such that the chromatograph runs a sample with a mobile phase including at least the compound and having an eluent profile corresponding to the particular eluent profile.

* * * * *